United States Patent
Knappe et al.

(10) Patent No.: US 9,132,077 B2
(45) Date of Patent: *Sep. 15, 2015

(54) COSMETIC AGENT

(75) Inventors: Thorsten Knappe, Schenefeld (DE); Marcus Noll, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 272 days.

This patent is subject to a terminal disclaimer.

(21) Appl. No.: 13/359,587

(22) Filed: Jan. 27, 2012

(65) Prior Publication Data

US 2012/0128619 A1    May 24, 2012

Related U.S. Application Data

(63) Continuation of application No. PCT/EP2010/060296, filed on Jul. 16, 2010.

(30) Foreign Application Priority Data

Jul. 28, 2009  (DE) .......................... 10 2009 028 054

(51) Int. Cl.
*A61Q 5/06* (2006.01)
*A61Q 5/00* (2006.01)
*A61K 8/81* (2006.01)

(52) U.S. Cl.
CPC ............. *A61K 8/8164* (2013.01); *A61K 8/8152* (2013.01); *A61K 8/8158* (2013.01); *A61Q 5/06* (2013.01)

(58) Field of Classification Search
CPC ........... A61K 2800/594; A61K 8/8158; A61K 8/8164; A61K 8/817; A61K 2800/5424; A61K 8/042; A61K 8/046; A61K 8/06; A61K 8/732; A61K 2800/20; A61K 8/022; A61K 8/11; A61K 8/25; A61K 8/86; A61K 8/891

See application file for complete search history.

(56) References Cited

U.S. PATENT DOCUMENTS 5,972,356 A * 10/1999 Peffly et al. ................... 424/401
2005/0204484 A1 * 9/2005 Meder et al. ...................... 8/405

* cited by examiner

*Primary Examiner* — Audrea Buckley
(74) *Attorney, Agent, or Firm* — David K. Benson

(57) ABSTRACT

A cosmetic agent particularly useful for the styling of keratin fibers such as human hair is disclosed. The cosmetic agent of the present invention contains a unique combination of specific amphoteric polymers with an amphiphilic anionic polymer that imparts optimized properties to the agent without additional active ingredients. Styling agents containing this inventive polymer combination provide a very high degree of hold and moisture resistance to keratinous fibers without compromising flexibility.

13 Claims, No Drawings

COSMETIC AGENT

CROSS-REFERENCE TO RELATED APPLICATIONS

This application is a continuation of PCT Application Serial No. PCT/EP2010/060296, filed on Jul. 16, 2010, which claims priority under 35 U.S.C. §119 to 10 2009 028 054.5 (DE) filed on Jul. 28, 2009. The disclosures PCT/EP2010/060296 and DE 10 2009 028 054.5 are hereby incorporated by reference in their entirety.

FIELD OF THE INVENTION

The present invention relates to cosmetic agents containing a special combination of polymers and the use of these agents in particular for temporary shaping of keratinic fibers.

BACKGROUND OF THE INVENTION

Keratinic fibers are understood in principle to include all animal hair, for example, wool, horsehair, angora hair, furs, feathers and products or textiles produced therefrom. However, human hair comprises the keratinic fibers receiving the most attention in the context of cosmetic agents.

The use of polymers in a wide variety of cosmetic agents is widespread. They are used in agents for treating skin and in agents for treating hair, in agents that are washed off or out again immediately after use, so-called rinse-off products, as well as in agents which remain on the skin or hair, so-called leave-on agents. The polymers are used for a wide variety of reasons here, and certain properties of the polymers are utilized in each case. The thickening or care properties of the polymers are often of primary concern in agents for treating skin, in shampoos, hair rinses and hair treatments. In addition to these properties, especially film-forming effects and/or hair-setting effects are demanded in agents for temporary shaping of keratinic fibers, hereinafter also referred to as styling agents. Polymers frequently also serve as auxiliary means for improving the deposition and fixation of other active ingredients and ingredients on the skin or hair or making it possible at all. For example, by adding suitable polymers to hair coloring agents, the rubbing fastness and stability of the covering can be increased.

Cosmetic agents usually contain individual polymers tailored specifically to achieve a very specific effect. If various effects are to be achieved, it is necessary to add several polymers. However, if too many different polymers are used, this may entail a number of disadvantages. For example, problems may occur in formulation, e.g., because the polymers are reacting with one another or with other ingredients of the agent, resulting in precipitation or decomposition. Certain polymers also tend to be deposited on the skin and in particular on the hair, so that they are no longer completely removed in an ordinary washing and an unwanted accumulation of the polymer occurs and thus ultimately there is a burden on the hair or skin.

Therefore there is always a demand for polymers or suitable combinations of a few polymers which have as many of the desired properties as possible at the same time.

For example, in the case of styling agents it is necessary for the polymers to impart the strongest possible hold to the treated hair. In addition to a high degree of hold, however, styling agents must also fulfill a number of other requirements. These may be subdivided roughly into properties involving the hair, properties involving the respective formulation, for example, properties of the foam, the gel or the spray aerosol and properties affecting the handling of the styling agent, with special importance being attributed to the properties involving the hair. In particular the humidity resistance, low tackiness and a balanced conditioning effect may be mentioned. Furthermore, a styling agent should be universally usable for all types of hair if possible. If the styling agent is a gel or a paste, the polymers should also have thickening properties.

PCT Application Publication WO2008/052886 discloses that a combination of special zwitterionic polymers and film-forming and/or hair-setting amphoteric polymers has self-thickening properties, and that the film-forming and/or hair-setting properties of the individual polymers are increased. However, problems nevertheless occur in thickening in particular when providing thickened agents, i.e., highly viscous cosmetic agents using this polymer combination. In particular the stability of thickened cosmetic agents in storage and providing thickened and transparent agents with this polymer combination are areas that need improvement.

The object of the present invention was therefore to make available suitable polymer combinations that impart optimized properties to the cosmetic agents even without the addition of further active ingredients. In particular cosmetic agents are to be thickened with the aforementioned polymer combination in a manner so that they are stable in storage while at the same time having good film-forming properties and/or hair-setting properties. Styling agents containing these polymers should have a very high degree of hold without having to do without flexibility and good moisture resistance—in particular resistance to perspiration and water. Production of stable viscous and stable transparent cosmetic compositions using this polymer combination should be made possible in particular.

SUMMARY OF THE INVENTION

It has now been surprisingly found that by using a unique combination of certain amphoteric polymers with an amphiphilic anionic polymer, optimized properties may be imparted to cosmetic agents even without additional active ingredients. Styling agents containing these inventive polymer combinations give a very high degree of hold and moisture resistance without compromising flexibility.

In an exemplary embodiment, the present invention is a cosmetic agent comprising in a cosmetically acceptable carrier:

(a) at least one copolymer formed from:

(i) at least one monomer A1 selected from acrylic acid, methacrylic acid, acrylic acid alkyl esters, and methacrylic acid alkyl esters; and (ii) at least one amphoteric monomer A2 selected from (meth)acryloyl alkyl amine oxides of formula A2-I,

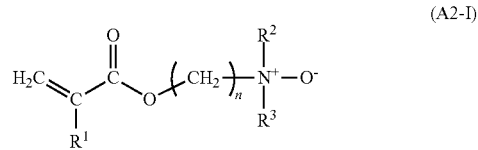

(A2-I)

and (meth)acryloyl alkyl betaines of formula A2-II,

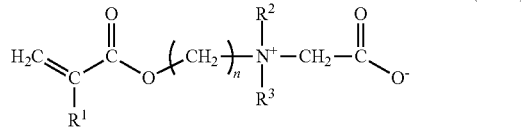

(A2-II)

wherein in formulas A2-I and A2-II: $R^1$ stands for H or $CH_3$; $R^2$ and $R^3$ each, independently of one another, stand for optionally branched $C_{1-10}$ alkyl; and n stands for an integer from 1 to 20;
(b) at least one film-forming and/or hair-setting amphoteric polymer B which is different from copolymer A; and
(c) at least one amphiphilic anionic polymer C formed from at least one monomer of formula C1 and at least one itaconic acid ester monomer of formula C2,

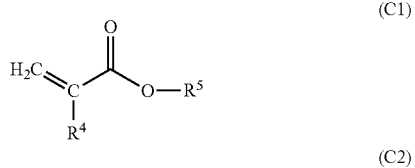

(C1)

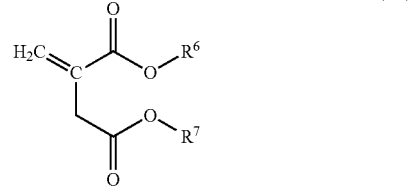

(C2)

wherein $R^4$ stands for a hydrogen atom or a methyl group; $R^5$ stands for a hydrogen atom or a ($C_1$ to $C_4$) alkyl group; $R^6$ and $R^7$ denote a hydrogen atom provided that at least one radical of $R^6$ and $R^7$ stands for a group $-A^1-R^8$, wherein $A^1$ stands for a group $*—(CH_2CH_2O)_x—*$ in which x stands for an integer from 5 to 35, a group $*—(CH_2CHMeO)_y—*$, wherein y stands for an integer from 5 to 35 or a group $*—(CH_2CH_2O)_x—(CH_2CHMeO)_y—*$, wherein the sum of x+y stands for an integer from 5 to 35 and x and y are greater than zero; and $R^8$ stands for a ($C_6$ to $C_{30}$) alkyl group.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

With that said, the present invention is a cosmetic agent comprising in a cosmetically acceptable carrier:
(a) at least one copolymer formed from:
  (i) at least one monomer A1 selected from acrylic acid, methacrylic acid, acrylic acid alkyl esters, and methacrylic acid alkyl esters; and
  (ii) at least one amphoteric monomer A2 selected from (meth)acryloyl alkyl amine oxides of formula A2-I,

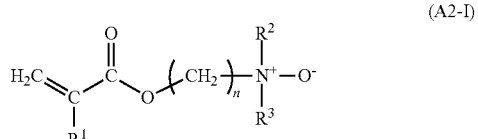

(A2-I)

and (meth)acryloyl alkyl betaines of formula A2-II,

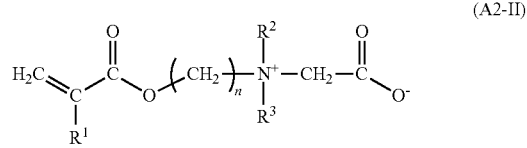

(A2-II)

wherein in formulas A2-I and A2-II: $R^1$ stands for H or $CH_3$; $R^2$ and $R^3$ each, independently of one another, stand for optionally branched $C_{1-10}$ alkyl; and n stands for an integer from 1 to 20;
(b) at least one film-forming and/or hair-setting amphoteric polymer B which is different from copolymer A; and
(c) at least one amphiphilic anionic polymer C formed from at least one monomer of formula C1 and at least one itaconic acid ester monomer of formula C2,

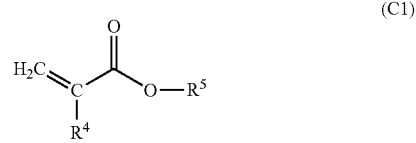

(C1)

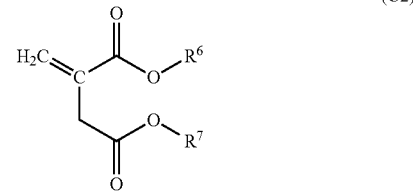

(C2)

wherein $R^4$ stands for a hydrogen atom or a methyl group; $R^5$ stands for a hydrogen atom or a ($C_1$ to $C_4$) alkyl group; $R^6$ and $R^7$ denote a hydrogen atom provided that at least one radical of $R^6$ and $R^7$ stands for a group $-A^1-R^8$, wherein $A^1$ stands for a group $*—(CH_2CH_2O)_x—*$ in which x stands for an integer from 5 to 35, a group $*—(CH_2CHMeO)_y—*$, wherein y stands for an integer from 5 to 35 or a group $*—(CH_2CH_2O)_x—(CH_2CHMeO)_y—*$, wherein the sum of x+y stands for an integer from 5 to 35 and x and y are greater than zero; and $R^8$ stands for a ($C_6$ to $C_{30}$) alkyl group.

Film-forming amphoteric and/or hair-setting amphoteric polymers B are known. The same also holds for copolymers A and their use as film-forming and/or hair-setting polymers.

The cosmetic agents according to the invention contain at least one copolymer A as the first obligatory component.

Copolymers A formed from the aforementioned monomers are understood in the sense of the present invention to include only those copolymers which contain in addition to polymer units resulting from the incorporation of the aforementioned monomers A1 and A2 into the copolymer, max. 5 wt %, preferably max. 1 wt % polymer units attributed to the incorporation of other monomers. The copolymers A are exclusively composed of polymer units resulting from the incorporation of the aforementioned monomers A1 and A2 into the copolymer.

Preferred monomers A1 include acrylic acid, methacrylic acid, acrylic acid $C_{1-20}$ alkyl esters and methacrylic acid $C_{1-20}$ alkyl esters.

Monomer A1 is especially preferably selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid lauryl ester, methacrylic acid lauryl ester, acrylic acid cetyl ester, methacrylic acid cetyl ester, acrylic acid stearyl ester and methacrylic acid stearyl ester, most especially preferably from acrylic acid, methacrylic acid, acrylic acid methyl ester, methacrylic acid methyl ester, acrylic acid ethyl ester, methacrylic acid ethyl ester, acrylic acid lauryl ester, methacrylic acid lauryl ester, acrylic acid stearyl ester and methacrylic acid stearyl ester.

Preferred monomers A2 include (meth)acryloyl alkyl amine oxides of formula A2-I and/or (meth)acryloxyl alkyl betaines of formula A2-II, wherein $R^2$ and $R^3$, independently of one another, each stand for methyl, ethyl, propyl, isopropyl, butyl, isobutyl, isobutyl or tert-butyl, especially preferably for methyl.

Preferred monomers A2 are also selected from at least one monomer from the group formed from (meth)acryloyl alkyl amine oxides of the formula A2-I and/or (meth)acryloyl alkyl betaines of the formula A2-II, wherein n stands for an integer from 1 to 5, preferably for an integer from 1 to 3, and especially preferably for 2.

Monomers A2 are preferably also selected from at least one monomer from the group formed from (meth)acryloyl alkyl amine oxides of the formula A2-I and/or (meth)acryloyl alkyl betaines of the formula A2-II, wherein $R^1$ stands for $CH_3$.

The monomers A2 are especially preferably selected from at least one monomer from the group formed from (meth)acryloyl alkyl amine oxides of the formula A2-I and/or (meth)acryloyl alkyl betaines of the formula A2-II, wherein $R^2$ and $R^3$, independently of one another, each stand for methyl, ethyl, propyl, isopropyl, butyl, isobutyl or tert-butyl, especially preferably for methyl, n stands for an integer from 1 to 5, preferably for an integer from 1 to 3 and especially preferably for 2, and $R^1$ stands for $CH_3$.

Monomer A2 is most especially preferably selected from at least one monomer from the group formed from (meth)acryloyl alkyl amine oxides of the formula A2-I and/or (meth)acryloyl alkyl betaines of the formula A2-II, wherein $R^1$, $R^2$ and $R^3$ each stand for $CH_3$ and n stands for 2.

In all the embodiments described above, it is again preferable for the copolymer (A) to be formed from (in particular exclusively) at least one monomer of the formula (A1) and at least one of the monomers of formula A2-I corresponding to the respective embodiment.

In a preferred embodiment, the agent according to the invention contains at least one copolymer A derived from the copolymerization of (i) least one monomer A1 selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester; and (ii) methacryloyl ethyl betaine as monomer A2.

Corresponding copolymers are known and are available, for example, under the designations Diaformer® Z-400, Diaformer® Z-AT, Diaformer® Z-301N, Diaformer® Z-SM and Diaformer® Z-W from the company Clariant and under the designations Yukaformer® 202, Yukaformer® 204, Yukaformer® 206 and Yukaformer® 301 from Mitsubishi. The use of Diformer® Z-301N is especially preferred.

In a more preferred embodiment, the agent according to the invention contains at least one copolymer A formed from at least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2 methacryloylethylamine oxide, in particular methacryloylethyl-N,N-dimethylamine oxide (in formula A2-I: $R^1=CH_3$, n=2, $R^2$ and $R^3=CH_3$).

These copolymers are also known and are available under the brand name Diaformer® Z-632 from the company Clariant, for example, but the use of Diaformer® Z-632 is especially preferred.

In a preferred embodiment, the agent according to the invention contains at least one copolymer A formed from at least three monomers A1, wherein the first monomer is selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, the second monomer being selected from acrylic acid lauryl ester and methacrylic acid lauryl ester and the third monomer is selected from acrylic acid stearyl ester and methacrylic acid stearyl ester; and as monomer A2 methacryloylethylamine oxide, in particular methacryloylethyl-N,N-dimethylamine oxide (in formula (A24): $R^1=CH_3$, n=2, $R^2$ and $R^3=CH_3$).

Corresponding copolymers are also known and are available, for example, under the brand names Diaformer® Z-611, Diaformer® Z-612, Diaformer® Z-613, Diaformer® Z-631, Diaformer® Z-633, Diaformer® Z-651, Diaformer® Z-711N, Diaformer® Z-712N and Diaformer® Z-731N from Clariant, with Diaformer® Z-712N and Diaformer® Z-651 preferred.

It is of course also possible for the agents according to the invention to contain a mixture of at least two of copolymers A which are used according to the three preferred embodiments just described.

The agents according to the invention contain copolymer A, preferably in an amount of 0.01 to 20 wt %, especially preferably 0.05 to 10 wt %, and most especially preferably 0.1 to 5 wt %, based on the total agent.

The agents according to the invention may of course also contain several copolymers A, but the total amount of copolymer A preferably does not exceed 20 wt %.

The copolymers A can be produced from the aforementioned monomers by means of the known polymerization methods and are usually available commercially.

The agents according to the invention for temporary shaping of keratinic fibers contain as the second obligatory component at least one film-forming and/or hair-setting amphoteric polymer B, which is different from copolymer A.

The film-forming and/or hair-setting amphoteric polymer B is preferably selected from the group of copolymers of monomers with carboxyl groups and/or sulfonic groups, in particular acrylic acid, methacrylic acid, itaconic acid and monomers with amino groups in particular monoalkyl aminoalkyl acrylates, dialkyl aminoalkyl acrylates, monoalkyl aminoalkyl methacrylates, dialkylamino alkyl methacrylates, monoalkyl aminoalkyl acrylamides, dialkyl aminoalkyl acrylamides, monoalkyl aminoalkyl methacrylamides, dialkyl aminoalkyl methacrylamides and the copolymers of N-octylacrylamide, methyl methacrylate, hydroxypropyl methacrylate, N-tert-butylaminoethyl methacrylate and acrylic acid.

The agent according to the invention especially preferably contains an N-octylacrylamide/acrylic acid/tert-butylamino ethyl methacrylate copolymer, in particular preferably the copolymer distributed under the brand name Amphomer® (INCI designation octylacrylamide/acrylates/butylaminoethyl methacrylate copolymer) by the company National Starch as the film-forming and/or hair-setting amphoteric polymer B.

The film-forming and/or hair-setting amphoteric polymer B is preferably present in an amount of 0.01 to 20 wt %, preferably 0.1 to 15 wt %, especially preferably 1.0 to 10 wt %, based on the total agent. Multiple film-forming and/or hair-setting amphoteric polymers B may of course also be present, but the total amount of film-forming and/or hair-setting amphoteric polymers B preferably does not exceed 20 wt %.

To achieve the desired properties of the agent according to the invention, the agent must contain both copolymer A and a film-forming and/or hair-setting amphoteric polymer B which is different from copolymer A. In particular the combination of very strong hold and excellent humidity resistance which is desired for styling agents can be obtained in this way. It has been found that an optimal profile of properties is obtained when the agent contains copolymer A and the film-forming and/or hair-setting amphoteric polymer B in a weight ratio of 1:50 to 20:1, preferably 1:30 to 10:1, especially preferably 1:20 to 5:1, most especially preferably 1:10 to 2:1. An excess of copolymer A improves the thickening properties of the polymer mixture.

Furthermore, the agent according to the invention contains as the third obligatory component at least one amphiphilic anionic polymer C. This amphiphilic anionic polymer C is different from copolymer A and from the film-forming amphoteric and/or hair-setting amphoteric polymer B.

The term "amphiphilic" herein refers to a molecule that comprises both hydrophilic and lipophilic properties. An "amphiphilic polymer" is understood to be a polymer that comprises both hydrophilic structural elements and lipophilic structural elements bonded to the polymer backbone.

The $A^1R^8$ radical of the itaconic acid ester monomer of formula (C2) is of course bound to the radical molecule via the carbon atom from $A^1$, and $R^8$ binds to the oxygen terminus of $A^1$.

Preferred amphiphilic anionic polymers C are formed exclusively from at least one said monomer of formula C1 and at least one monomer of said formula C2.

Preferred amphiphilic anionic polymers C include those wherein at least one radical from $R^6$ and $R^7$ stands for a group $*$-$A^1$-$R^8$ and the other radical stands for a hydrogen atom, wherein $A^1$ and $R^8$ are defined above.

Especially preferred amphiphilic anionic polymers C for use in the present agent are characterized in being formed from at least one monomer of formula C1 and at least one itaconic acid ester monomer of formula of C2:

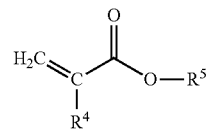

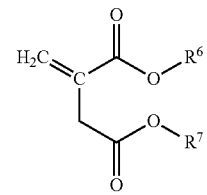

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group $*$—$(CH_2CH_2O)_x$—$*$, with x an integer from 5 to 35 (in particular for an integer from 10 to 30); and $R^8$ denotes a ($C_6$ to $C_{30}$) alkyl group.

Furthermore, amphiphilic anionic polymers C are preferably selected from acrylates/ceteth-20 itaconate copolymer (e.g., which can be obtained as Structure® 3001 from the company Akzo Nobel), acrylates/palmeth-25 itaconate copolymer (e.g., which can be obtained as Polygel W30® or Polygel W40® from the company 3V Sigma), acrylates/Stearet-20 itaconate copolymer (e.g., which can be obtained as Structure® 2001 from the company Akzo Nobel).

Preferred agents are characterized in that they have a viscosity of 1000 to 500,000 mPa·s, preferably from 5000 to 300,000 mPa·s, especially preferably from 10,000 to 150,000 mPa·s (each measured with the Brookfield RVDV II+ with Heilpath, spindle T-E, 5 rpm, 20° C.).

Preferred agents contain the amphiphilic anionic polymer C in an amount of 0.1 to 10 wt %, based on the weight of the agent.

An especially preferred embodiment of the present invention is therefore a cosmetic agent containing in a cosmetically acceptable carrier:

(a) at least one copolymer formed from:
  (i) at least one monomer A1 selected from acrylic acid, methacrylic acid, acrylic acid alkyl esters, and methacrylic acid alkyl esters; and
  (ii) at least one amphoteric monomer A2 selected from (meth)acryloyl alkyl amine oxides of formula A2-I,

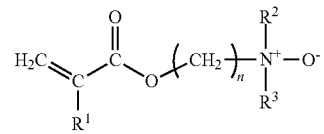

wherein $R^1$ stands for H or $CH_3$ (preferably methyl); $R^2$ and $R^3$ each, independently of one another, stand for optionally branched $C_{1-10}$ alkyl; and n stands for an integer from 1 to 4 (preferably 2);

(b) at least one film-forming amphoteric and/or hair-setting amphoteric polymer B, different from copolymer A, selected from octylacrylamide/acrylates/butylaminoethyl methacrylate copolymer; and (c) at least one amphiphilic anionic polymer C formed from at least one monomer of formula C1 and at least one itaconic acid ester monomer of formula C2, (C1)

$$\underset{R^4}{\overset{H_2C}{\Longleftarrow}}\overset{O}{\underset{C}{\bigvee}}O-R^5$$

(C2)

$$H_2C\underset{\displaystyle\bigvee}{\overset{O}{\Longleftarrow}}\overset{O}{\underset{\displaystyle\bigvee}{\bigcup}}\overset{O}{\underset{O}{\bigcup}}R^6$$
$$\phantom{H_2C=}\phantom{\bigvee}\phantom{\bigcup}O-R^7$$

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30), a group *—$(CH_2CHMeO)_y$—*, wherein y stands for an integer from 5 to 35, or a group *—$(CH_2CH_2O)_x$—$(CH_2CHMeO)_y$—*, wherein the sum of x+y stands for an integer from 5 to 35 and x and y are greater than zero; and $R^8$ denotes a ($C_6$ to $C_{30}$) alkyl group.

An especially preferred embodiment of the present invention is in turn a cosmetic agent containing in a cosmetically acceptable carrier:

(a) at least one copolymer A formed from at least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2, methacryloylethylamine oxide, in particular methacryloylethyl-N,N-dimethylamine oxide (in formula A2-I: $R^1$=$CH_3$, n=2, $R^2$ and $R^3$=$CH_3$);

(b) at least one film-forming amphoteric and/or hair-setting amphoteric polymer B which is different from copolymer A and is selected from octylacrylamide/acrylates/butylaminoethyl meth-acrylate copolymer; and (c) at least one amphiphilic anionic polymer C formed from at least one monomer of formula C1 and at least one itaconic acid ester monomer of formula C2, (C1)

$$\underset{R^4}{\overset{H_2C}{\Longleftarrow}}\overset{O}{\underset{C}{\bigvee}}O-R^5$$

(C2)

$$H_2C\underset{\displaystyle\bigvee}{\overset{O}{\Longleftarrow}}\overset{O}{\underset{\displaystyle\bigvee}{\bigcup}}\overset{O}{\underset{O}{\bigcup}}R^6$$
$$\phantom{H_2C=}\phantom{\bigvee}\phantom{\bigcup}O-R^7$$

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30), a group *—$(CH_2CHMeO)_y$—*, wherein y stands for an integer from 5 to 35, or a group *—$(CH_2CH_2O)_n$—$(CH_2CHMeO)_y$—*, wherein the sum of x+y stands for an integer from 5 to 35 and x and y are greater than zero; and $R^8$ denotes a ($C_6$ to $C_{30}$) alkyl group.

An especially preferred embodiment of the present invention is in turn a cosmetic agent containing in a cosmetically acceptable carrier:

(a) at least one copolymer A formed from at least one monomer A1 selected from acrylic acid, methacrylic acid, acrylic acid alkyl esters and methacrylic acid alkyl esters and at least one amphoteric monomer A2 selected from (meth)acryloyl alkyl amine oxides of formula A2-I, (A2-I)

$$H_2C\underset{R^1}{\overset{O}{\Longleftarrow}}\overset{O}{\underset{C}{\bigvee}}O\text{---}(CH_2)_n\text{---}\underset{R^3}{\overset{R^2}{\underset{|}{N^+}}}\text{---}O^-$$

wherein $R^1$ stands for H or $CH_3$ (in particular $CH_3$); $R^2$ and $R^3$ each, independently of one another, stand for optionally branched $C_{1-10}$ alkyl; and n stands for an integer from 1 to 4 (in particular 2);

(b) at least one film-forming amphoteric and/or hair-setting amphoteric polymer B, different from copolymer A, selected from octylacrylamide/acrylates/butylaminoethyl meth-acrylate copolymer; and (c) at least one amphiphilic anionic polymer C formed from at least one monomer of formula (C1) and at least one itaconic acid ester monomer of formula (C2), (C1)

$$\underset{R^4}{\overset{H_2C}{\Longleftarrow}}\overset{O}{\underset{C}{\bigvee}}O-R^5$$

(C2)

$$H_2C\underset{\displaystyle\bigvee}{\overset{O}{\Longleftarrow}}\overset{O}{\underset{\displaystyle\bigvee}{\bigcup}}\overset{O}{\underset{O}{\bigcup}}R^6$$
$$\phantom{H_2C=}\phantom{\bigvee}\phantom{\bigcup}O-R^7$$

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30); and $R^8$ denotes a ($C_6$ to $C_{30}$) alkyl group.

An especially preferred embodiment of the present invention is in turn a cosmetic agent containing in a cosmetically acceptable carrier:

(a) at least one copolymer A formed from least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester and as monomer A2 methacryloylethylamine oxide, in particular methacryloylethyl-N,N-dimethylamine oxide (in formula A2-I: $R^1=CH_3$, n=2, $R^2$ and $R^3=CH_3$);

(b) at least one film-forming amphoteric and/or hair-setting amphoteric polymer B, different from copolymer A, selected from octylacrylamide/acrylates/butylaminoethyl meth-acrylate copolymer; and (c) at least one amphiphilic anionic polymer C formed from at least one monomer of formula (C1) and at least one itaconic acid ester monomer of formula (C2),

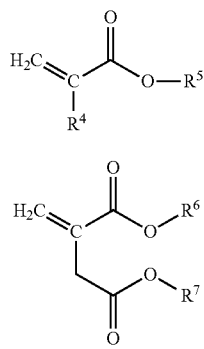

wherein $R^4$ denotes hydrogen or a methyl group; $R^5$ denotes hydrogen or a ($C_1$ to $C_4$) alkyl group; at least one of $R^6$ and $R^7$ is the group $-A^1-R^8$ while the other of $R^6$ and $R^7$ is hydrogen, wherein $A^1$ denotes the group $*-(CH_2CH_2O)_x-*$, with x an integer from 5 to 35 (in particular for an integer from 10 to 30); and $R^8$ denotes a ($C_6$ to $C_{30}$) alkyl group.

An especially preferred embodiment of the present invention is therefore a cosmetic agent having a viscosity of 1000 to 500,000 mPa·s, preferably from 5000 to 300,000 mPa·s, especially preferably from 10,000 to 150,000 mPa·s (each measured with the Brookfield RVDV II+ with Heilpath, spindle T-E, 5 rpm, 20° C.), containing in a cosmetically acceptable carrier:

(a) at least one copolymer A formed from least one monomer A1 selected from acrylic acid, methacrylic acid, acrylic acid alkyl esters and methacrylic acid alkyl esters and at least one amphoteric monomer A2 selected from (meth)acryloyl alkyl amine oxides of formula A2-I,

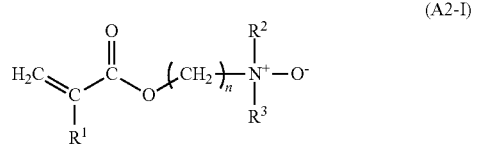

wherein $R^1$ stands for H or $CH_3$ (in particular $CH_3$); $R^2$ and $R^3$ each, independently of one another, stand for optionally branched $C_{1-10}$ alkyl; and n stands for an integer from 1 to 4 (in particular 2);

(b) at least one film-forming amphoteric and/or hair-setting amphoteric polymer B, which is different from copolymer A and is selected from octylacrylamide/acrylates/butylaminoethyl meth-acrylate copolymer; and (c) at least one amphiphilic anionic polymer C formed from at least one monomer of formula (C1) and at least one itaconic acid ester monomer of formula (C2),

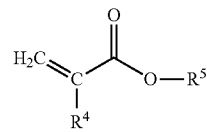

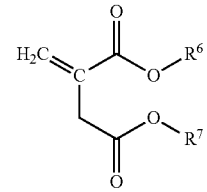

wherein $R^4$ denotes hydrogen or a methyl group; $R^5$ denotes hydrogen or a ($C_1$ to $C_4$) alkyl group; at least one of $R^6$ and $R^7$ is the group $-A^1-R^8$ while the other of $R^6$ and $R^7$ is hydrogen, wherein $A^1$ denotes the group $*-(CH_2CH_2O)_x-*$, with x an integer from 5 to 35 (in particular for an integer from 10 to 30), a group $-(CH_2CHMeO)_y-*$, wherein y stands for an integer from 5 to 35, or a group $-(CH_2CH_2O)_x-(CH_2CHMeO)_y-*$, wherein the sum of x+y stands for an integer from 5 to 35 and x and y are greater than zero; and $R^8$ denotes a ($C_6$ to $C_{30}$) alkyl group.

An especially preferred embodiment of the present invention is in turn a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from least two monomers: A1 the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and, monomer A2 methacryloylethylamine oxide, in particular methacryloylethyl-N,N-dimethylamine oxide (in formula A2-I: $R^1=CH_3$, n=2, $R^2$ and $R^3=CH_3$);

(b) at least one film-forming amphoteric and/or hair-setting amphoteric polymer B, different from copolymer A selected from octylacrylamide/acrylates/butylaminoethyl meth-acrylate copolymer; and (c) at least one amphiphilic anionic polymer C formed from at least one monomer of formula (C1) and at least one itaconic acid ester monomer of formula (C2),

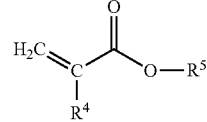

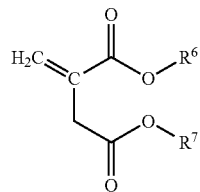 (C2)

wherein $R^4$ denotes hydrogen or a methyl group; $R^5$ denotes hydrogen or a ($C_1$ to $C_4$) alkyl group; at least one of $R^6$ and $R^7$ is the group $-A^1-R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30), a group —$(CH_2CHMeO)_y$—*, wherein y stands for an integer from 5 to 35, or a group —$(CH_2CH_2O)_x$—$(CH_2CHMeO)_y$—*, wherein the sum of x+y stands for an integer from 5 to 35 and x and y are greater than zero; and $R^8$ denotes a ($C_6$ to $C_{30}$) alkyl group.

An especially preferred embodiment of the present invention is in turn a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from at least one monomer A1 selected from acrylic acid, methacrylic acid, acrylic acid alkyl esters and methacrylic acid alkyl esters; and at least one amphoteric monomer A2 selected from (meth)acryloyl alkyl amine oxides of formula A2-I,

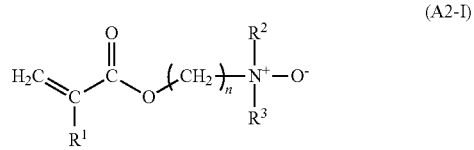 (A2-I)

wherein $R^1$ stands for H or $CH_3$ (in particular $CH_3$); $R^2$ and $R^3$ each, independently of one another, stand for optionally branched $C_{1-10}$ alkyl; and n stands for an integer from 1 to 4 (in particular 2);

(b) at least one film-forming amphoteric and/or hair-setting amphoteric polymer B, which that is different from copolymer A and is selected from octylacrylamide/acrylates/butylaminoethyl methacrylate copolymer; and (c) at least one amphiphilic anionic polymer C formed from at least one monomer of formula (C1) and at least one itaconic acid ester monomer of formula (C2),

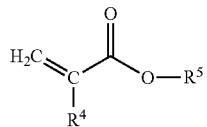 (C1)

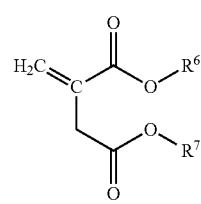 (C2)

wherein $R^4$ denotes hydrogen or a methyl group; $R^5$ denotes hydrogen or a ($C_1$ to $C_4$) alkyl group; at least one of $R^6$ and $R^7$ is the group $-A^1-R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30); and $R^8$ denotes a ($C_6$ to $C_{30}$) alkyl group.

An especially preferred embodiment of the present invention is in turn a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2 methacryloylethylamine oxide, in particular methacryloylethyl-N,N-dimethylamine oxide (in formula A2-I: $R^1=CH_3$, n=2, $R^2$ and $R^3=CH_3$);

(b) at least one film-forming amphoteric and/or hair-setting amphoteric polymer B different from copolymer A selected from octylacrylamide/acrylates/butylaminoethyl meth-acrylate copolymer; and (c) at least one amphiphilic anionic polymer C formed from at least one monomer of formula (C1) and at least one itaconic acid ester monomer of formula (C2),

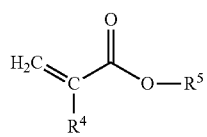 (C1)

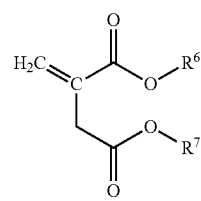 (C2)

wherein $R^4$ denotes hydrogen or a methyl group; $R^5$ denotes hydrogen or a ($C_1$ to $C_4$) alkyl group; at least one of $R^6$ and $R^7$ is the group $-A^1-R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30); and $R^8$ denotes a ($C_6$ to $C_{30}$) alkyl group.

Each of the aforementioned preferred embodiments is in turn preferably transparent.

In addition to copolymer A and amphiphilic anionic polymers C and film-forming and/or hair-setting amphoteric polymers B, the agents may additionally contain any other known film-forming and/or hair-setting polymer. These film-forming and/or hair-setting polymers may be either permanently or temporarily cationic, anionic or nonionic.

The polymers are often multifunctional, but their functions are not always clearly and unambiguously differentiable from one another. This is true in particular of film-forming and hair-setting polymers. However, it is pointed out explicitly here that both film-forming and hair-setting polymers are essential within the scope of the present invention. Since these two properties are not completely independent of one another, the term "hair-setting polymers" should also always be understood as "film-forming polymers" and vice versa.

The preferred properties of the film-forming polymers include film formation. Film-forming properties are understood to be polymers which leave a continuous film on skin, hair or nails on drying. Such film-forming substances may be used in a wide variety of cosmetic products such as, for example, face masks, makeup, hair-setting products, hair sprays, hair gels, hair waxes, hair treatments, shampoos or nail polish. In particular those polymers which have a sufficient solubility in alcohol or water/alcohol mixtures to be present in completely dissolved form in the agent according to the invention are preferred. The film-forming polymers may be of a synthetic or natural origin.

Film-forming polymers are additionally understood according to the invention to include polymers capable of depositing a transparent polymer film on the hair when used in 0.01 to 20 wt % aqueous, alcoholic or aqueous-alcoholic solution.

Additional suitable synthetic film-forming hair-setting polymers include, for example, homopolymers or copolymers composed of at least one of the following monomers: vinyl pyrrolidone, vinyl caprolactam, vinyl esters, for example, vinyl acetate, vinyl alcohol, acrylamide, methacrylamide, alkyl and dialkyl acrylamide, alkyl and dialkyl methacrylamide, alkyl acrylate, alkyl methacrylate, propylene glycol or ethylene glycol, where the alkyl groups of these monomers are preferably $C_1$ to $C_7$ alkyl groups, especially preferably $C_1$ to $C_3$ alkyl groups.

Examples that can be mentioned include homopolymers of vinyl caprolactam, vinyl pyrrolidone or N-vinylformamide. Other suitable synthetic film-forming hair-setting polymers include, for example, the copolymers of vinyl pyrrolidone and vinyl acetate, terpolymers of vinyl pyrrolidone, vinyl acetate and vinyl propionate, polyacrylamides, which are distributed, for example, under the brand names Akypomine® P 191 from the company CHEM-Y, Emmerich or Sepigel® 305 from the company Seppic; polyvinyl alcohols, which are distributed, for example, under the brand names Elvanol® by Du Pont or Vinol® 523/540 by the company Air Products as well as polyethylene glycol/polypropylene glycol copolymers distributed, for example, under the brand name Ucon® of Union Carbide.

Suitable natural film-forming polymers include, for example, cellulose derivatives, e.g., hydroxypropyl cellulose with a molecular weight of 30,000 to 50,000 g/mol, which are distributed, for example, under the brand name Nisso SI® by the company Lehmann & Voss, Hamburg.

Hair-setting polymers contribute to the hold and/or creation of the hair volume and hair body of the overall hair style. The aforementioned hair-setting polymers are at the same time also film-forming polymers and therefore in general are typical substances for styling hair treatment agents such as hair-setting agents, hair mousse, hair wax, hair sprays. The film-forming may therefore be in spots or may bond only a few fibers together.

Substances which also impart hydrophobic properties to hair are preferred here because they reduce the tendency of hair to absorb humidity, i.e., water. Therefore limp hair strands are reduced and thus a long-lasting hair style creation and hold are ensured. The test method used for this frequently is the so-called curl retention test. These polymer substances may also be incorporated successfully into leave-on and rinse-off hair treatments or shampoos. Since polymers are often multifunctional, i.e., manifest multiple effects, which are desired for application technology, there are numerous polymers in several groups divided according to their mechanism of action, e.g., in the CTFA Handbook.

If the agents according to the invention contain additional film-forming and/or hair-setting polymers, they are preferably used in an amount of 0.01 to 20 wt %, preferably 0.1 to 15 wt %, based on the total hair-setting agent. Multiple film-forming and/or hair-setting polymers may of course also be present, in which case the total amount of other film-forming and hair-setting polymers is preferably max. 20 wt %, however.

An especially preferred embodiment of the present invention is a cosmetic agent containing in a cosmetically acceptable carrier:

(a) at least one copolymer A formed from: at least one monomer A1 selected from acrylic acid, methacrylic acid, acrylic acid alkyl esters and methacrylic acid alkyl esters; and at least one amphoteric monomer A2 selected from (meth)acryloyl alkyl amine oxides of formula A2-I,

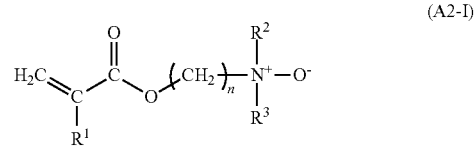

wherein $R^1$ stands for H or $CH_3$ (in particular $CH_3$); $R^2$ and $R^3$ each, independently of one another, stand for optionally branched $C_{1-10}$ alkyl; and n stands for an integer from 1 to 4 (in particular 2);

(b) at least one film-forming amphoteric and/or hair-setting amphoteric polymer B that is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

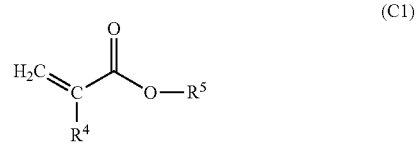

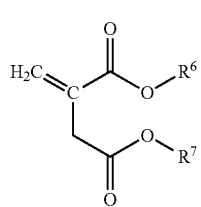

(C2)

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30), a group —$(CH_2CHMeO)_y$—*, wherein y stands for an integer from 5 to 35, or a group —$(CH_2CH_2O)_x$—$(CH_2CHMeO)_y$—*, wherein the sum of x+y stands for an integer from 5 to 35 and x and y are greater than zero; and $R^8$ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is in turn a cosmetic agent containing in a cosmetically acceptable carrier:

(a) at least one copolymer A formed from least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2 methacryloylethylamine oxide, in particular methacryloylethyl-N,N-dimethylamine oxide (in formula A2-I: $R^1$=$CH_3$, n=2, $R^2$ and $R^3$=$CH_3$);

(b) at least one film-forming amphoteric and/or hair-setting amphoteric polymer B, which is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

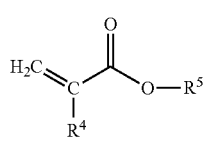

(C1)

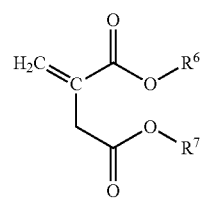

(C2)

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30), a group —$(CH_2CHMeO)_y$—*, wherein y stands for an integer from 5 to 35, or a group —$(CH_2CH_2O)_x$—$(CH_2CHMeO)_y$—*, wherein the sum of x+y stands for an integer from 5 to 35 and x and y are greater than zero; and $R^8$ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is in turn a cosmetic agent containing in a cosmetically acceptable carrier:

(a) at least one copolymer A formed from at least one monomer A1 selected from acrylic acid, methacrylic acid, acrylic acid alkyl esters and methacrylic acid alkyl esters; and at least one amphoteric monomer A2 selected from (meth)acryloyl alkyl amine oxides of formula A2-I,

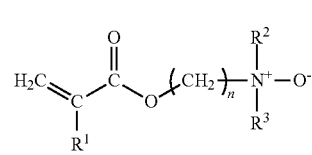

(A2-I)

wherein $R^1$ stands for H or $CH_3$ (in particular $CH_3$); $R^2$ and $R^3$ each, independently of one another, stand for optionally branched $C_{1-10}$ alkyl; and n stands for an integer from 1 to 4 (in particular 2);

(b) at least one film-forming amphoteric and/or hair-setting amphoteric polymer B, which that is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

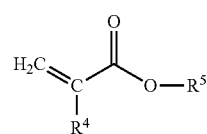

(C1)

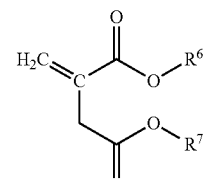

(C2)

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30); and $R^8$ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is in turn a cosmetic agent containing in a cosmetically acceptable carrier:

(a) at least one copolymer A formed from: at least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2 methacryloylethylamine oxide, in particular methacryloylethyl-N,N-dimethylamine oxide (in formula A2-I: $R^1$=$CH_3$, n=2, $R^2$ and $R^3$=$CH_3$);

(b) at least one film-forming amphoteric and/or hair-setting amphoteric polymer B, which is different from copolymer A and is selected from octylacrylamide/acrylates/butylaminoethyl meth-acrylate copolymer;

(c) at least one amphiphilic anionic polymer C formed from at least one monomer of formula (C1) and at least one itaconic acid ester monomer of formula (C2),

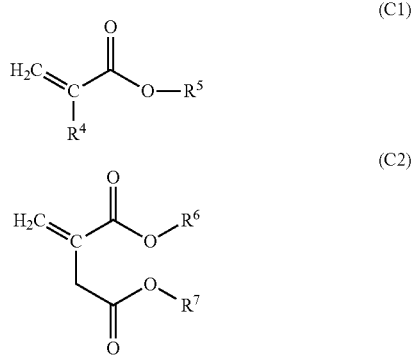

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30); and $R^8$ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is therefore a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from: least one monomer A1 selected from acrylic acid, methacrylic acid, acrylic acid alkyl esters and methacrylic acid alkyl esters; and at least one amphoteric monomer A2 selected from (meth)acryloyl alkyl amine oxides of formula A2-I,

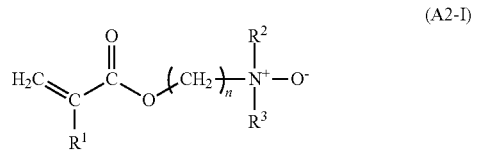

wherein $R^1$ stands for H or $CH_3$ (in particular $CH_3$); $R^2$ and $R^3$ each, independently of one another, stand for optionally branched $C_{1-10}$ alkyl; and n stands for an integer from 1 to 4 (in particular 2);

(b) at least one film-forming amphoteric and/or hair-setting amphoteric polymer B, which is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

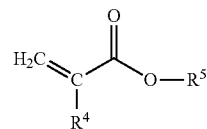

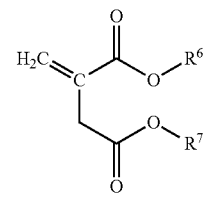

wherein $R^4$ denotes hydrogen or a methyl group; $R^5$ denotes hydrogen or a ($C_1$ to $C_4$) alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30), a group —$(CH_2CHMeO)_y$—*, wherein y stands for an integer from 5 to 35, or a group —$(CH_2CH_2O)_x$—$(CH_2CHMeO)_y$—*, wherein the sum of x+y stands for an integer from 5 to 35 and x and y are greater than zero; and $R^8$ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is in turn a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from: least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2 methacryloylethylamine oxide, in particular methacryloylethyl-N,N-dimethylamine oxide (in formula A2-I: $R^1$=$CH_3$, n=2, $R^2$ and $R^3$=$CH_3$);

(b) at least one film-forming amphoteric and/or hair-setting amphoteric polymer B, which is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

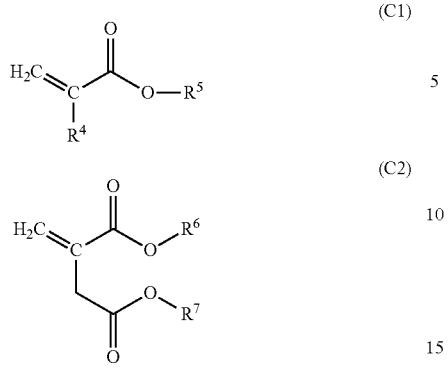

(C1)

(C2)

wherein R⁴ denotes hydrogen or a methyl group; R⁵ denotes hydrogen or a ($C_1$ to $C_4$) alkyl group; at least one of R⁶ and R⁷ is the group -A¹-R⁸ while the other of R⁶ and R⁷ is hydrogen, wherein A¹ denotes the group *—$(CH_2CH_2O)_x$—*, with x an integer from 5 to 35 (in particular for an integer from 10 to 30), a group —$(CH_2CHMeO)_y$—*, wherein y stands for an integer from 5 to 35, or a group —$(CH_2CH_2O)_x$—$(CH_2CHMeO)_y$—*, wherein the sum of x+y stands for an integer from 5 to 35 and x and y are greater than zero; and R⁸ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is in turn a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from: at least one monomer A1 selected from acrylic acid, methacrylic acid, acrylic acid alkyl esters and methacrylic acid alkyl esters; and at least one amphoteric monomer A2 selected from (meth)acryloyl alkyl amine oxides of formula A2-I,

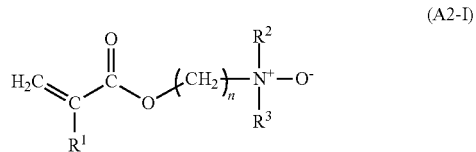

(A2-I)

wherein R¹ stands for H or $CH_3$ (in particular $CH_3$); R² and R³ each, independently of one another, stand for optionally branched $C_{1-10}$ alkyl; and n stands for an integer from 1 to 4 (in particular 2);

(b) at least one film-forming amphoteric and/or hair-setting amphoteric polymer B, which is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

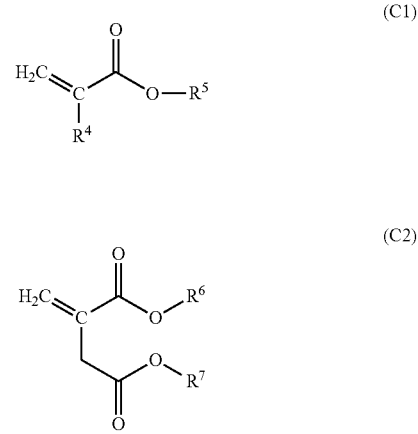

(C1)

(C2)

wherein R⁴ denotes hydrogen or a methyl group; R⁵ denotes hydrogen or a ($C_1$ to $C_4$) alkyl group; at least one of R⁶ and R⁷ is the group -A¹-R⁸ while the other of R⁶ and R⁷ is hydrogen, wherein A¹ denotes the group *—$(CH_2CH_2O)_x$—*, with x an integer from 5 to 35 (in particular for an integer from 10 to 30); and R⁸ denotes a ($C_6$ to $C_{30}$) alkyl group; and (d) polyvinyl pyrrolidone and/or N-vinyl pyrrolidone/vinyl acetate copolymer.

An especially preferred embodiment of the present invention is in turn a cosmetic agent having a viscosity of 1000 to 500,000 mPa·s, preferably from 5000 to 300,000 mPa·s, especially preferably from 10,000 to 150,000 mPa·s (each measured using the Brookfield RVDV II+ with the Heilpath, spindle T-E, 5 rpm, 20° C.), containing in a cosmetically acceptable carrier:

(a) at least one copolymer A formed from: at least two monomers A1, the first monomer being selected from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer being selected from acrylic acid stearyl ester and methacrylic acid stearyl ester; and as monomer A2 methacryloylethylamine oxide, in particular methacryloylethyl-N,N-dimethylamine oxide (in formula A2-I: R¹=$CH_3$, n=2, R² and R³=$CH_3$);

(b) at least one film-forming amphoteric and/or hair-setting amphoteric polymer B, which is different from copolymer A and is selected from octylacrylamide/acrylates/butylaminoethyl methacrylate copolymer;

(c) at least one amphiphilic anionic polymer C formed from at least one monomer of formula (C1) and at least one itaconic acid ester monomer of formula (C2),

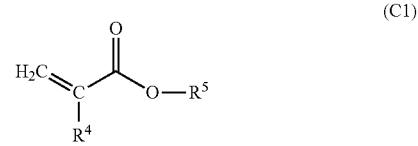

(C1)

-continued

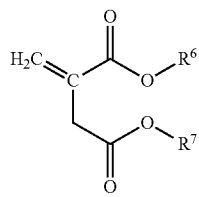

(C2)

wherein $R^4$ denotes hydrogen or a methyl group; $R^5$ denotes hydrogen or a ($C_1$ to $C_4$) alkyl group; at least one of $R^6$ and $R^7$ is the group $-A^1-R^8$ while the other of $R^6$ and $R^7$ is hydrogen, wherein $A^1$ denotes the group *—$(CH_2CH_2O)_x$—*, with x an integer from 5 to 35 (in particular for an integer from 10 to 30); and $R^8$ denotes a ($C_6$ to $C_{30}$) alkyl group; and
(d) polyvinyl pyrrolidone and/or N-vinyl pyrrolidone/vinyl acetate copolymer.

All the aforementioned preferred embodiments are again preferably transparent.

The agents according to the invention contain the polymers in a cosmetically acceptable carrier.

Preferred cosmetically acceptable carriers include aqueous, alcoholic or aqueous-alcoholic media, preferably with at least 10 wt % water, based on a total agent. The alcohols present may include in particular low alcohols with 1 to 4 carbon atoms, for example, ethanol and isopropanol, which are generally used for cosmetic purposes in particular.

Additional co-solvents that may be used include organic solvents or a mixture of solvents with a boiling point below 400° C. in an amount of 0.1 to 15 wt %, preferably 1 to 10 wt %, based on the total agent. Especially suitable as additional co-solvents are unbranched or branched hydrocarbons, such as pentane, hexane, isopentane and cyclic hydrocarbons such as cyclopentane and cyclohexane. Additional especially preferred water-soluble solvents include glycerol, ethylene glycol and propylene glycol in an amount of up to 30 wt %, based on the total agent.

These agents preferably have a pH of 4.5 to 6.9. The pH range is especially preferably between 6 and 6.9. The information about the pH value in the sense of this patent application relates to the pH value at 25° C., unless otherwise noted. Agents having these preferred pH values have an especially good humidity resistance of the set hair style.

The agents according to the invention may also contain the excipients and additives which are usually added to the respective cosmetic agents.

Suitable excipients and additives include in particular care substances. These are used in both hair and skin treatment agents and may be incorporated into creams, shampoos, hair rinses, hair treatments, gels, pump and aerosol sprays and foam products for example, given a suitable choice of the care substance.

The agents according to the invention may also contain the excipient and additives which are usually added to traditional styling agents.

In particular additional care substances are to be mentioned as suitable excipients and additives.

An example of a care substance that may be used is silicone oil and/or a silicone gum.

Silicone oils or silicone gums that are suitable according to the invention include in particular dialkyl and alkylaryl siloxanes, for example, dimethyl polysiloxane and methyl phenyl polysiloxane as well as their alkoxylated, quaternized or anionic derivatives. Cyclic and linear polydialkyl siloxanes, their alkoxylated and/or aminated derivatives, dihydroxy polydimethyl siloxanes and polyphenyl alkyl siloxanes are preferred.

Silicone oils produce a wide variety of effects. For example, they influence both dry combability and wet combability at the same time, the feel of dry and wet hair as well as its luster. Those skilled in the art understand the term silicone oils to include several structures of organic silicon compounds. This is understood first to include the dimethiconols.

The following commercial products are mentioned as examples of such products: Botanisil NU150M (Botanigenics), Dow Corning 1-1254 fluid, Dow Corning 2-9023 fluid, Dow Corning 2-9026 fluid, ultrapure dimethiconol (Ultra Chemical), Unisil SF-R (Universal Preserve), X-21-5619 (ShinEtsu Chemical Co.), Abil OSW 5 (Degussa Care Specialties), ACC DL-9430 emulsion (Taylor Chemical Company), AEC dimethiconol and sodium dodecylbenzene sulfonate (A & E Connock (Perfumery & Cosmetic, Ltd.), B C dimethiconol emulsion 95 (Basildon Chemical Company, Ltd.), cosmetic fluid 1401, cosmetic fluid 1403, cosmetic fluid 1501, cosmetic fluid 1401DC (all the aforementioned are from Chemsil Silicones, Inc.), Dow Corning 1401 fluid, Dow Corning 1403 fluid, Dow Corning 1501 fluid, Dow Corning 1784 HVF emulsion, Dow Corning 9546 silicone elastomer blend (all the aforementioned are from Dow Corning Corporation), Dub Gel Si 1400 (Stearinerie Dubois Fils), HVM 4852 emulsion (Crompton Corporation), Jeesilc 6056 (Jeen International Corporation), Lubrasil, Lubrasil DS (both from Guardian Laboratories), Nonychosine E, Nonychosine V (both from Exsymol), SanSurf Petrolatum-25, Satin Finish (both from Collaborative Laboratories, Inc.), Silatex-D30 (Cosmetic Ingredient Resources), Silsoft 148, Silsoft E-50, Silsoft E-623 (all the aforementioned are from Crompton Corporation), SM555, SM2725, SM2765, SM2785 (all the aforementioned are from GE Silicones), Taylor T-Sil CD-1, Taylor TME-4050E (all from Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforementioned are from WackerChemie GmbH).

Dimethicones form the second group of silicones which may be present according to the invention. They may be both linear and branched as well as cyclic or cyclic and branched.

Dimethicone polyols form another group of silicones which are suitable. Corresponding dimethicone copolyols are commercially available and are distributed, for example, by the company Dow Corning under the brand name Dow Corning® 5330 fluid.

The teaching according to the invention of course also includes the fact that the dimethiconols, dimethicones and/or dimethicone copolymers may already be present in the form of an emulsion. After preparing the corresponding dimethiconols, dimethicones and/or dimethicone copolyols, the corresponding emulsion of dimethiconols, dimethicones and/or dimethicone copolyols can be produced from them and the usual methods of emulsification with which those skilled in the art are familiar. Both cationic, anionic, nonionic or zwitterionic surfactants and emulsifiers may be used here as excipients for producing the corresponding emulsions. The emulsions of dimethiconols, dimethicones and/or dimethicone copolyols may of course also be prepared directly by emulsion polymerization methods. Those skilled in the art are very familiar with such methods.

If the dimethiconols, dimethicones and/or dimethicone copolyols are used as emulsions, then the droplet size of the emulsified particles according to the invention is 0.01 to 10,000 μm, preferably 0.01 to 100 μm, especially preferably 0.01 to 20 μm and most especially preferably 0.01 to 10 μm. The particle size is determined according to the light scatter method.

If branched dimethiconols, dimethicones and/or dimethicone copolyols are used, this is understood to mean that the branching is greater than a random branching which occurs randomly due to impurities in the respective monomers. In the sense of the present invention, branched dimethiconols, dimethicones and/or dimethicone copolyols are therefore understood to mean that the degree of branching is greater than 0.01%. A degree of branching greater than 0.1% and most especially preferably greater than 0.5% is preferred. The degree of branching is determined from the ratio of the unbranched monomers to the branching monomers, i.e., the quantity of trifunctional and tetrafunctional siloxanes. According to the invention, both low-branched and high-branched dimethiconols, dimethicones and/or dimethicone copolyols may be most especially preferred.

Especially suitable silicones are amino-functional silicones in particular the silicones combined under the INCI designation amodimethicones. It is therefore preferred according to the invention if the agents according to the invention additionally contain at least one amino-functional silicone. These are understood to include silicones having at least one optionally substituted amino group. These silicones are referred to according to the INCI Declaration as amodimethicones and are available, for example, in the form of an emulsion as commercial product Dow Corning® 939 or as the commercial product Dow Corning® 949 in mixture with a cationic surfactant and a nonionic surfactant.

Such amino-functional silicones, which have an amine number above 0.25 meq/g, preferably above 0.3 meq/g and in particular preferably above 0.4 meq/g are preferred. The amine number stands for milliequivalents of amine per gram of amino-functional silicone, which can be determined by titration and may also be reported in units of mg KOH/g.

These agents preferably contain the silicones in amounts of 0.01 wt % to 15 wt %, especially preferably from 0.05 to 2 wt %, based on the total agent.

The agent may contain, for example, at least one protein hydrolysate and/or another derivative as a care substance of another class of compounds.

Protein hydrolysates are product mixtures obtained by acid-catalyzed, base-catalyzed or enzymatically catalyzed degradation of proteins. The term "protein hydrolysates" is also understood according to the invention to refer to total hydrolysates as well as individual amino acids and their derivatives as well as mixtures of different amino acids. The molecular weight of the protein hydrolysates that can be used according to the invention is between 75 Dalton, which is the molecular weight of glycine, and 200,000 Dalton, but the molecule is preferably 75 to 50,000 Dalton and most especially preferably 75 to 20,000 Dalton.

According to the invention, protein hydrolysates of either plant or animal or marine or synthetic origin may be used.

Animal protein hydrolysates include, for example, elastin, collagen, keratin, silk and milk protein hydrolysates which may also be present in the form of salts. Such products are distributed, for example, under the brand names Dehylan® (Cognis), Promois® (Interorgana), Collapuron® (Cognis), Nutrilan (Cognis), Gelita-Sol® (Deutsche Gelatine Fabriken Stoess & Co.), Lexein® (Inolex), Sericin (Pentapharm) and Kerasol® (Croda).

The protein hydrolysates are present in the agents according to the invention, for example, in concentrations of 0.01 wt % to 20 wt %, preferably 0.05 wt % to 15 wt % and most especially preferably 0.05 wt % to 5 wt %, each based on the total application preparation.

The agents according to the invention may also contain at least one vitamin, a provitamin, a vitamin precursor and/or one of their derivatives as the care substance.

According to the invention, vitamins, provitamins and vitamin precursors which are usually assigned to the groups A, B, C, E, F and H are preferred.

The agents according to the invention preferably contain vitamins, provitamins and vitamin precursors from the groups A, B, C, E and H. Panthenol, pantolactone, pyridoxine and its derivatives as well as nicotinamide and biotin are especially preferred.

D-Panthenol, optionally in combination with at least one of the aforementioned silicone derivatives, is most especially preferred as a care substance.

The addition of panthenol, like the addition of glycerol and/or propylene glycol, increases the flexibility of the polymer film formed in use of the agents according to the invention. Thus, if a particularly flexible hold is desired, the agents according to the invention may contain panthenol instead of or in addition to glycerol and/or propylene glycol. In a preferred embodiment the agents according to the invention contain panthenol, preferably in an amount of 0.05 to 10 wt %, especially preferably 0.1 to 5 wt %, each based on the total agent.

The agents according to the invention may additionally contain at least one plant extract as the care substance.

These extracts are usually prepared by extraction of the total plant. However, in individual cases it may also be preferred to produce the extracts exclusively from flowers and/or leaves of the plants.

In particular the extracts from green tea, oak bark, stinging nettle, witch hazel, hops, henna, chamomile, burdock root, horsetail, hawthorne, lime-tree blossoms, almond, aloe vera, pine needle, horse chestnut, sandalwood, juniper berry, coconut, mango, apricot, lime, wheat, kiwi, melon, orange, grapefruit, sage, rosemary, birch, mallow, lady's smock, wild thyme, yarrow, thyme, melissa, rest harrow, coltsfoot, marsh mallow, meristem, ginseng and ginger root are preferred according to the invention.

In addition, it may be preferable to use mixtures of several different plant extracts, in particular two different plant extracts in the agents according to the invention.

Monosaccharides and/or oligosaccharides may also be used as the care substance in the agents according to the invention.

Both monosaccharides and oligosaccharides, for example, cane sugar, lactose and raffinose may be used. The use of monosaccharides is preferred according to the invention. The monosaccharides are in turn understood to include those compounds having 5 or 6 carbon atoms.

Suitable pentoses and hexoses include, for example, ribose, arabinose, xylose, lyxose, allose, altrose, glucose, mannose, gulose, idose, galactose, talose, fucose and fructose. Arabinose, glucose, galactose and fructose are the preferred carbohydrates for use here. Glucose is most especially preferred here and is suitable in both the D-(+)- and L-(−)-configurations or as a racemate.

In addition, derivatives of these pentoses and hexoses such as the corresponding onic and uronic acids (sugar acids), sugar alcohols and glycosides may also be used according to the invention. Preferred sugar acids include gluconic acid, glucuronic acid, sugar acid, mannose sugar acid and mucic acid. Preferred sugar alcohols include sorbitol, mannitol and dulcitol. Preferred glycosides are the methyl glycosides.

Since the monosaccharides and/or oligosaccharides used are usually obtained from natural raw materials such as starch, they usually have the configurations corresponding to these raw materials (e.g., D-glucose, D-fructose and D-galactose).

The monosaccharides and/or oligosaccharides are preferably used in the agents according to the invention in an amount of 0.1 to 8 wt %, especially preferably 1 to 5 wt %, based on the total application preparation.

These agents may also contain at least one lipid as the care substance.

Suitable lipids according to the invention include phospholipids, for example, soy lecithin, egg lecithin and kephalins, as well as the substances known by the INCI designations linoleamidopropyl PG dimonium chloride phosphate, cocamidopropyl PG dimonium chloride phosphate and stearamidopropyl PG dimonium chloride phosphate. These products are distributed, for example, by the company Mona under the brand names Phospholipid EFA®, Phospholipid PTC and Phospholipid SV®. The agents according to the invention contain the lipids preferably in amount of 0.01 to 10 wt %, in particular 0.1 to 5 wt %, based on the total application preparation Oil substances are also suitable as the care substance.

The natural and synthetic cosmetic oil substances include for example:

1. Vegetable oils sunflower oil, olive oil, soy oil, canola oil, almond oil, jojoba oil, orange oil, wheat germ oil, peach pit oil and the liquid fractions of coconut oil. However, other triglyceride oils such as the liquid fractions of beef tallow and synthetic triglyceride oils are also suitable;
2. Liquid paraffin oils, isoparaffin oils and synthetic hydrocarbons as well as di-n-alkyl ether with a total between 12 and 36 carbon atoms, in particular 12 to 24 carbon atoms, such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-undecyl ether, n-undecyl-n-dodecyl ether and n-hexyl-n-undecyl ether as well as di-tert-butyl ether, diisopentyl ether, di-3-ethyldecyl ether, tert-butyl-n-octyl ether, isopentyl-n-octyl ether and 2-methylpentyl-n-octyl ether. The compounds 1,3-di-(2-ethylhexyl)-cyclohexane (Cetiol® S) and di-n-octyl ether (Cetiol® OE), which can be obtained as commercial products may be preferred;
3. Ester oils, understood to include the esters of $C_6$-$C_{30}$ fatty acids with $C_2$-$C_{30}$ fatty alcohols. The monoesters of fatty acids with alcohols with 2 to 24 carbon atoms are preferred. Especially preferred according to the invention are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V);
4. Dicarboxylic acid esters such as di-n-butyl adipate, di(2-ethylhexyl) adipate, di(2-ethylhexyl)succinate and diisotridecyl acetate as well as diol esters such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate;
5. Symmetrical, asymmetrical, or cyclic esters of carbonic acid with fatty alcohols, for example, as described in Unexamined German Patent DE-OS 197 56 454, glycerol carbonate or dicaprylyl carbonate (Cetiol® CC);
6. Trifatty acid esters of saturated and/or unsaturated, linear and/or branched fatty acids with glycerol;
7. Fatty acid partial glycerides including monoglycerides, diglycerides and their technical-grade mixtures. When using technical-grade products, small amounts of triglycerides may still be present due to the production process. The partial glycerides preferably conform to the formula (D4-I),

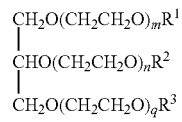

(D4-I)

wherein $R^1$, $R^2$ and $R^3$, independently of one another, stand for hydrogen or a linear or branched saturated and/or unsaturated acyl radical with 6 to 22 carbon atoms, preferably 12 to 18 carbon atoms, with the provision that at least one of these groups stands for an acyl radical and at least one of these groups stands for hydrogen. The sum (m+n+q) stands for 0 or for numbers from 1 to 100, preferably for 0 or 5 to 25. $R^1$ preferably stands for an acyl radical, and $R^2$ and $R^3$ stand for hydrogen, and the sum (m+n+q) is 0.

Typical examples include the mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, eleostearic acid, arachidic acid, gadoleic acid, behenic acid and erucaic acid as well as their technical-grade mixtures. Oleic acid monoglycerides are preferred for use here.

The use quantity of the natural and synthetic cosmetic oil substances in the agents according to the invention is usually 0.1-30 wt %, based on the total ready-to-use preparation, preferably 0.1-20 wt % and in particular 0.1-15 wt %.

Although each of the aforementioned care substances yields a satisfactory result when used alone, all embodiments in which the agent contains multiple care substances even from different groups are also included within the scope of the present invention.

By adding a UV filter, the agents themselves as well as the fibers to be treated can be protected from harmful influences of UV radiation. Therefore at least one UV filter is preferably added to the agent. The suitable UV filters are not subject to any general restrictions with regard to their structure and their physical properties. Instead, all the UV filters that can be used in the cosmetic field and whose absorption maximum is in the range of UVA (315-400 nm), in the UVB (280-315 nm) or UVC (<280 nm) range may be used. UV filters with an absorption maximum in the UVB range in particular in the range from approx. 280 to approx. 300 nm are especially preferred.

The UV filters preferred according to the invention may be selected from substituted benzophenones, p-aminobenzoic acid esters, diphenylacrylic acid esters, cinnamic acid esters, salicylic acid esters, benzimidazoles and o-aminobenzoic acid esters.

The UV filters are usually present in amounts of 0.01-5 wt %, based on the total ready-to-use preparations. Amounts of 0.1-2.5 wt % are preferred.

In a special embodiment, the agent according to the invention also contains one or more direct dyes. This makes it possible for the treated keratinic fibers to be not only temporarily structured but also to be dyed at the same time when using this agent. This may be desirable in particular if only a temporary coloration is desired, for example, with striking fashion colors, which can be removed again from the keratinic fibers by simply washing.

Direct dyes are usually nitrophenylenediamine, nitroamino phenols, azo dyes, anthraquinones or indophenols. Preferred direct dyes include the compounds known by the international designations i.e., brand names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52 as well as 1,4-diamino-2-nitrobenzene, 2-amino-4-nitrophenol, 1,4-bis-(6-hydroxyethyeamino-2-nitrobenzene, 3-nitro-4-(6-hydroxyethyl)aminophenol, 2-(2'-hydroxyethyl)amino-4,6-dinitrophenol, 1-(2'-hydroxyethyeamino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene. Cationic direct dyes are preferred.

Especially preferred for the present invention include (a) cationic triphenylmethane dyes, for example, Basic Blue 7, Basic Blue 26, Basic Violet 2 and Basic Violet 14; (b) aromatic systems substituted with a quaternary nitrogen group, for example, Basic Yellow 57, Basic Red 76, Basic Blue 99, Basic Brown 16 and Basic Brown 17; and, (c) direct dyes containing a heterocycle having at least one quaternary nitrogen atom, such as those mentioned in claims 6 through 11 of EP-A2-998 908, incorporated herein by reference.

The dyes which are also known by the names Basic Yellow 87, Basic Orange 31 and Basic Red 51 are most especially preferably cationic direct dyes of group (c). The cationic direct dyes distributed under the brand name Arianor® are also most especially preferred cationic direct dyes according to the invention.

The inventive agents according to this embodiment contain the direct dyes preferably in an amount of 0.001 to 20 wt %, based on the total agent.

It is preferable according to the invention for the inventive agents to be free of oxidative dye precursors. Oxidative dye precursors are divided into so-called developer components and coupler components. The developer components develop the actual dyestuff under the influence of oxidizing agents or atmospheric oxygen with one another or by coupling with one or more coupler components.

Depending on the type of agent according to the invention it may be necessary for them to contain at least one surfactant. This is true in particular of skin cleaning agents and shampoos. However, other agents such as hair rinses, hair cures and certain styling agents in particular styling foams may also contain surfactants.

For example, cationic surfactants such as those already described above as suitable care substances may be used. With regard to the preferred cationic surfactants and the quantities used, the statements made above are applicable accordingly.

In addition to or instead of the cationic surfactants, these agents may also contain additional surfactants or emulsifiers, but in principle both anionic and ampholytic as well as nonionic surfactants and all types of known emulsifiers are suitable. The group of ampholytic or amphoteric surfactants includes zwitterionic surfactants and ampholytes. The surfactants may already have an emulsifying effect.

Suitable anionic surfactants include in principle all the anionic surface-active substances that are suitable for use on the human body. These are characterized by a water-solubilizing anionic group, for example, a carboxylate, sulfate, sulfonate or phosphate group and a lipophilic alkyl group with approx. 8 to 30 carbon atoms. In addition, glycol or polyglycol ether groups, ester, ether and amide groups as well as hydroxyl groups may also be present in the molecule.

Examples of suitable anionic surfactants include, (each in the form of the sodium, potassium and ammonium salts as well as the mono-, di- and trialkanol ammonium salts with 2 to 4 carbon atoms in the alkanol group): (a) linear and branched fatty acids with 8 to 30 carbon atoms (soaps); (b) ether carboxylic acids of the formula R—O—$(CH_2CH_2O)_x$—$CH_2$—COOH in which R is a linear alkyl group with 8 to 30 carbon atoms and x=0 or 1 to 16; (c) acyl sarcosides with 8 to 24 carbon atoms in the acyl group; (d) acyl taurides with 8 to 24 carbon atoms in the acyl group; (e) acyl isethionates with 8 to 24 carbon atoms in the acyl group; (f) sulfosuccinic acid mono- and dialkyl esters with 8 to 24 carbon atoms in the alkyl group and sulfosuccinic acid monoalkylpolyoxyethyl esters with 8 to 24 carbon atoms in the alkyl group and 1 to 6 oxyethyl groups; (g) linear alkane sulfonates with 8 to 24 carbon atoms; (h) linear α-olefin sulfonates with 8 to 24 carbon atoms; (i) α-sulfo fatty acid ethyl esters of fatty acids with 8 to 30 carbon atoms; (j) alkyl sulfates and alkyl polyglycol ether sulfates of the formula R—$O(CH_2CH_2O)_x$—$OSO_3H$ in which R denotes a preferably linear alkyl group with 8 to 30 carbon atoms and x is 0 or 1 to 12; (k) mixtures of surface-active hydroxysulfonates; (l) sulfated hydroxyalkyl polyethylene and/or hydroxyalkylene propylene glycol ether; (m) sulfonates of unsaturated fatty acids with 8 to 24 carbon atoms and 1 to 6 double bonds; (n) esters of tartaric acid and citric acid with alcohols which are the addition products of approx. 2-15 molecules of ethylene oxide and/or propylene oxide onto fatty alcohols with 8 to 22 carbon atoms; (o) alkyl and/or alkenyl ether phosphates of the formula E1-I,

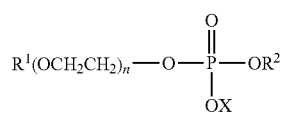

(E1-I)

wherein $R^1$ preferably stands for an aliphatic hydrocarbon radical with 8 to 30 carbon atoms, $R^2$ stands for hydrogen, a $(CH_2CH_2O)_n R^1$ radical or X, n stands for numbers from 1 to 10 and X stands for hydrogen, an alkali or alkaline earth metal or $NR^3R^4R^5R^6$, where $R^3$ to $R^6$ independently of one another stand for hydrogen or a $C_1$ to $C_4$ hydrocarbon radical; (p) sulfated fatty acid alkylene glycol esters of formula, $R^7CO(AlkO)_n SO_3M$, wherein $R^7CO$ stands for a linear or branched aliphatic saturated or unsaturated acyl radical with 6 to 22 carbon atoms, Alk stands for $CH_2CH_2$, $CHCH_3CH_2$ and/or $CH_2CHCH_3$, n stands for numbers from 0.5 to 5, and M stands for a cation such as those described in DE-OS 197 36 906; (q) amide ether carboxylic acids; and (r) condensation products of $C_8$ to $C_{30}$ fatty alcohols with protein hydrolysates and/or amino acids and their derivatives which are known to the skilled person as protein fatty acid condensates such as Lamepon products, Gluadin® products, Hostapon® KCG or Amisoft® products.

Preferred anionic surfactants include alkyl sulfates, alkyl polyglycol ether sulfates and ether carboxylic acids with 10 to 18 carbon atoms in the alkyl group and up to 12 glycol ether groups in the molecule, sulfosuccinic acid mono- and dialkyl esters with 8 to 18 carbon atoms in the alkyl group and sulfosuccinic acid monoalkylpolyoxyethyl esters with 8 to 18 carbon atoms in the alkyl group and 1 to 6 oxyethyl groups, monoglycerol disulfate, alkyl and alkenyl ether phosphates as well as protein fatty acid condensates.

Zwitterionic surfactants include those surface-active compounds having at least one quaternary ammonium group and at least one $COO^-$ or $SO_3^-$ group in the molecule. Especially suitable zwitterionic surfactants include the so-called betaines such as N-alkyl-N,N-dimethylammonium glycinates, for example, the coconut alkyl dimethylammonium glycinate, N-acylaminopropyl-N,N-dimethylammonium glycinate, for example, coconut acylaminopropyl dimethylammonium glycinate and 2-alkyl-3-carboxymethyl-3-hydroxyethyl imidazolines, each with 8 to 18 carbon atoms in the alkyl or acyl group, and coconut acylamino ethylhydroxyethyl carboxymethyl glycinate. A preferred zwitterionic surfactant is the fatty acid amide derivative known by the INCI designation cocamidopropyl betaine.

Ampholytes are understood to be those surface-active compounds which, besides having a $C_8$ to $C_{24}$ alkyl or acyl group in the molecule, also have at least one free amino group and at least one COOH or $SO_3H$ group and are capable of forming internal salts. Examples of suitable ampholytes include N-alkylglycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids and alkyl aminoacetic acids, each with approx. 8 to 24 carbon atoms in the alkyl group. Especially preferred ampholytes include N-coconut alkyl amino propionate, coconut acylaminoethyl amino propionate and $C_{12}$-$C_{18}$ acylsarcosine.

Nonionic surfactants contain as the hydrophilic group, for example, a polyol group, a polyalkylene glycol ether group or a combination of polyol and polyglycol ether group. Such compounds include, for example:

(a) addition products of 2 to 100 mol ethylene oxide and/or 1 to 5 mol propylene oxide onto linear and branched fatty alcohols with 8 to 30 carbon atoms, onto fatty acids with 8 to 30 carbon atoms and onto alkyl phenols with 8 to 15 carbon atoms in the alkyl group;
(b) end-group-capped addition products of 2 to 50 mol ethylene oxide and/or 1 to 5 mol propylene oxide onto linear and branched fatty alcohols with 8 to 30 carbon atoms, onto fatty acids with 8 to 30 carbon atoms and onto alkyl phenols with 8 to 15 carbon atoms in the alkyl group, with end group capping with a methyl group or a $C_2$ to $C_6$ alkyl group, such as for example those products obtainable under the brand names Dehydrol® LS, Dehydrol® LT (Cognis);
(c) $C_{12}$-$C_{30}$ fatty acid mono- and diesters of addition products of 1 to 30 mol ethylene oxide onto glycerol;
(d) addition products of 5 to 60 mol ethylene oxide onto castor oil and hydrogenated castor oil;
(e) polyol fatty acid esters, for example, the commercial product Hydagen® HSP (Cognis) or Sovermol products (Cognis);
(f) alkoxylated triglycerides;
(g) alkoxylated fatty acid alkyl esters of the formula, $R^1CO$—$(OCH_2CHR^2)_wOR^3$, in which $R^1CO$ stands for a linear or branched saturated and/or unsaturated acyl radical with 6 to 22 carbon atoms, $R^2$ stands for hydrogen or methyl, $R^3$ stands for linear or branched alkyl radicals with 1 to 4 carbon atoms, and w stands for numbers from 1 to 20;
(h) amine oxides;
(i) hydroxyl mixed ethers such as those described in DE-OS 19738866;
(j) sorbitan fatty acid esters and additional products of ethylene oxide onto sorbitan fatty acid esters such as polysorbates;
(k) sugar fatty acid esters and addition products of ethylene oxide onto sugar fatty acid esters;
(l) addition products of ethylene oxide onto fatty acid alkanolamide and fatty amines; and
(m) sugar surfactants of the type of alkyl and alkenyl oligoglycosides according to the formula, $R^4O$-$[G]_p$, where $R^4$ stands for alkyl or alkenyl radical with 4 to 22 carbon atoms, G stands for a sugar radical with 5 or 6 carbon atoms and p stands for numbers from 1 to 10. These can be obtained by the relevant methods of preparative organic chemistry.

The most especially preferred nonionic surfactants are the alkylene oxide addition products on the saturated linear fatty alcohols and fatty acids each with 2 to 100 mol ethylene oxide per mol fatty alcohol and/or fatty acid. Preparations with excellent properties are also obtained when they contain as nonionic surfactants $C_{12}$ to $C_{30}$ fatty acid monoesters and diesters of addition products of 1 to 30 mol ethylene oxide onto glycerol and/or addition products of 5 to 60 mol ethylene oxide onto castor oil and hydrogenated castor oil.

Agents according to the invention most especially preferably contain as the surfactant at least one addition product of 15 to 100 mol ethylene oxide, in particular 15 to 50 mol ethylene oxide, onto a linear or branched (in particular linear) fatty alcohol with 8 to 22 carbon atoms. These include most especially preferably ceteareth-15, ceteareth-25 or ceteareth-50, which are marketed as Eumulgin® CS 15 (Cognis), Cremophor A25 (BASF SE) and/or Eumulgin® CS 50 (Cognis).

The agents according to the invention they may be formulated in the products traditionally used for cosmetic agents, for example, in the form of solutions which may be applied to the skin or hair as facial preparations or hair water or pump or aerosol sprays, in the form of creams, emulsions, waxes, gels or foaming solutions containing surfactants or other preparations suitable for application to the skin or hair. The agents according to the invention are preferably present in gel form or cream form, with transparent gels being especially preferred.

The agents according to the invention are preferably agents for temporary shaping of keratinic fibers, i.e., styling agents. Preferred styling agents include styling gels and styling creams. Transparent styling gels are especially preferred.

Use of the agents according to the invention of the first subject matter of the invention for temporary shaping of keratinic fibers is a second subject matter of the present invention.

The agents and products containing these agents according to the invention are characterized in particular in that they impart a very strong and humidity-resistant styling hold to the treated hair.

The hold of the shaping, also known as styling hold, as well as the flexibility, elasticity and plasticity are determined according to the omega loop method in the sense of the present invention.

The quality of the transparency of a preparation according to the invention can be evaluated by visual observation of a doctored film on a sheet of glass.

The following examples should illustrate the subject matter of the present invention without restricting it in any way.

EXAMPLES

The following quantitative data are understood to be in percent by weight, unless otherwise indicated.

Styling gels denoted E1 to E5 in accordance with the present invention are set out in TABLE 1 below.

TABLE 1

Styling Gels

| Ingredients (wt. %) | Styling Gel Compositions | | | | |
|---|---|---|---|---|---|
| | E1 | E2 | E3 | E4 | E5 |
| 2-Amino-2-methylpropanol | — | 0.7 | 0.4 | 0.4 | 0.4 |
| Amphomer[1] | 1.5 | 3.0 | 2.5 | 4.0 | 4.0 |
| Dekafald[2] | — | — | — | 0.1 | — |
| Diaformer Z 632 N[3] | 0.5 | 0.5 | 6.0 | 2.0 | 8.0 |
| D-Panthenol | 0.2 | — | 0.1 | 0.2 | 0.2 |
| Ethanol | — | — | 5.0 | — | — |
| Ext. D & C Violet 2 | — | 0.00004 | — | — | — |
| Luviskol K 85 CQ[4] | — | 20.0 | — | — | — |
| Sodium hydroxide | 0.3 | — | — | — | — |
| Neolone PE[5] | — | 0.6 | — | — | — |
| Perfume | 0.1 | 0.2 | 0.4 | 0.2 | 0.2 |
| PEG-40 hydrogenated castor oil | 0.2 | 0.2 | 0.4 | 0.4 | 0.2 |
| 2-Phenoxyethanol | 0.9 | — | 0.9 | 0.5 | 0.9 |
| Polyethylene glycol MG 1500 | — | 2.0 | — | — | — |
| Polygel W 30[6] | 4.5 | 4.0 | 0.5 | 3.0 | 3.0 |
| Aculyn 22[7] | — | — | 5.0 | 1.0 | — |
| Uvinul P25 [8] | — | — | 0.1 | — | — |
| Water | to 100 | to 100 | to 100 | to 100 | to 100 |

Table Notes
(corresponding to superscripts at selected ingredients in TABLE 1):
[1]INCI designation: octylacrylamide/acrylates/butylaminoethyl methacrylate copolymer (Akzo Nobel);
[2]1,3-Dihydroxymethyl-5,5-dimethylhydantoin (approx. 54-56 wt % active substance in water; INCI designation: DMDM hydantoin) (Jan Dekker);
[3]Copolymerisate of stearyl acrylate, methacryloylethylamine oxide and one or more monomers of acrylic acid, methacrylic acid and their simple esters (28-32 wt % solid substance in ethanol; INCI designation: acrylates/stearyl acrylate/ethylamine oxide methacrylate copolymer) (Clariant);
[4]Polyvinylpyrrolidone (approx. 20% solid substance in water, preserved with approx. 250 ppm polyaminopropyl biguanide; INCI designation: PVP) (BASF SE);
[5]2-Methyl-2H-isothiazolin-3-one (approx. 1.55% in 2-phenoxyethanol; INCI designation: phenoxyethanol, methyl isothiazolinone) (Rohm and Haas);
[6]INCI designation: acrylates/palmeth-25 itaconate copolymer (3V Sigma);
[7]Copolymer of (meth)acrylic acid, (meth)acrylic acid ester and Steareth-20 methacrylic acid ester (29.5-30.5 wt % solid substance in water; INCI designation: acrylates/steareth- 20 methacrylate copolymer (Rohm and Haas); and
[8] 4-Aminobenzoic acid ethyl ester + 25 mol ethylene oxide (INCI designation: PEG-25 PABA) (BASF SE).

Even without the addition of the usual thickeners or structurants, styling agents on an aqueous and/or ethanolic basis having the desired transparent gel form and an excellent hold are obtained by the usual mixing of the raw materials listed in the table. In addition, these gels have an excellent transparency and their viscosity and transparency are stable in storage at temperatures from −15° C. up to +45° C.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:
1. A cosmetic agent comprising:
   a. at least one copolymer A, which is a copolymer of monomer units consisting of stearyl acrylate, methylacryloylethylamine oxide, and one or more monomers of acrylic acid, methacrylic acid and their esters;
   b. at least one film-forming and/or hair-setting amphoteric polymer B different from copolymer A; and
   c. at least one amphiphilic anionic polymer C comprising at least one monomer of formula C1 and at least one itaconic acid ester monomer of formula C2,

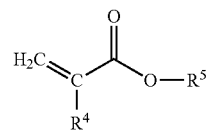

(C1)

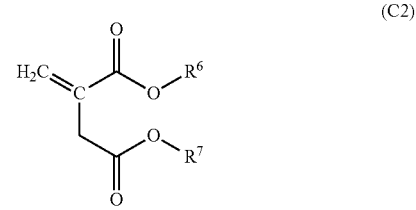

(C2)

wherein $R^4$ denotes hydrogen or a methyl group; $R^5$ denotes hydrogen or a $C_1$ to $C_4$ alkyl group; at least one of $R^6$ and $R^7$ is the group $-A^1-R^8$ while the other of $R^6$ and $R^7$ is hydrogen, wherein $A^1$ denotes the group $*-(CH_2CH_2O)_x-*$ with x an integer from 5 to 35, the group $*-(CH_2CHMeO)_y-*$ with y an integer from 5 to 35, or the group $*-(CH_2CH_2O)_x-(CH_2CHMeO)_y-*$ with the sum of x+y an integer from 5 to 35 and x and y each not zero; and, $R^8$ is a $C_6$ to $C_{30}$ alkyl group,
wherein the cosmetic agent is a transparent hair styling gel or cream.

2. The cosmetic agent of claim 1, wherein said copolymer A is present wherein it contains copolymer A in an amount of 0.01 to 20 wt % based on the total weight of the cosmetic agent composition.

3. The cosmetic agent of claim 2, wherein said copolymer A is present from 0.1 to 5 wt % based on the total weight of the cosmetic agent composition.

4. The cosmetic agent of claim 1, wherein said polymer B is present in an amount of 0.01 to 20 wt % based on the total weight of the cosmetic agent composition.

5. The cosmetic agent of claim 4, wherein said polymer B is present in an amount of 1.0 to 10 wt % based on the total weight of the cosmetic agent composition.

6. The cosmetic agent of claim 1, wherein said amphiphilic polymer C is present in an amount of 0.1 to 10 wt % based on the total weight of the cosmetic agent composition.

7. The cosmetic agent of claim 1, wherein said film-forming and/or hair-setting amphoteric polymer B comprising monomers having functionalities chosen from the group consisting of carboxyl groups, sulfonic groups, amino groups, amide groups, and mixtures thereof.

8. The cosmetic agent of claim 7, wherein said monomers are chosen from the group consisting of acrylic acid, methacrylic acid, itaconic acid, monoalkyl aminoalkyl acrylates, dialkyl aminoalkyl acrylates, monoalkyl aminoalkyl methacrylates, dialkyl aminoalkyl methacrylates, monoalkyl aminoalkyl acrylamides, dialkyl aminoalkyl acrylamides, monoalkyl aminoalkyl methacrylamides, dialkyl aminoalkyl methacrylamides, and mixtures thereof.

9. The cosmetic agent of claim 7, wherein said polymer B comprises copolymers of N-octylacrylamide, methyl methacrylate, hydroxypropyl methacrylate, N-tert-butylaminoethyl methacrylate, and acrylic acid.

10. The cosmetic agent of claim 7, wherein polymer B is N-octyl acrylamide/acrylic acid/tert-butyl aminoethyl methacrylate copolymer.

11. A cosmetic agent comprising:
   a. at least one copolymer A, which is a copolymer of monomer units consisting of stearyl acrylate, methylacryloylethylamine oxide, and one or more monomers of acrylic acid, methacrylic acid and their esters;
   b. at least one film-forming and/or hair-setting amphoteric polymer B different from copolymer A; and
   c. at least one amphiphilic anionic polymer C comprising at least one monomer of formula C1 and at least one itaconic acid ester monomer of formula C2,

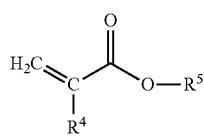
(C1)

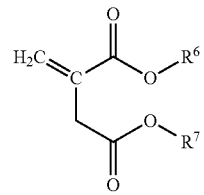
(C2)

wherein $R^4$ denotes hydrogen or a methyl group; $R^5$ denotes hydrogen or a $C_1$ to $C_4$ alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—* with x an integer from 5 to 35; and, $R^8$ denotes a $C_6$ to $C_{30}$ alkyl group,
wherein the cosmetic agent is a transparent composition.

12. A cosmetic agent including a polymer combination, said polymer combination consisting essentially of:
   a. from 0.1 to 5 wt % of at least one copolymer A, which is a copolymer of monomer units consisting of stearyl acrylate, methylacryloylethylamine oxide, and one or more monomers of acrylic acid, methacrylic acid and their esters;
   b. from 1 to 10 wt % of at least one film-forming and/or hair-setting amphoteric polymer B different from copolymer A; and
   c. from 0.1 to 10 wt % of at least one amphiphilic anionic polymer C comprising at least one monomer of formula C1 and at least one itaconic acid ester monomer of formula C2,

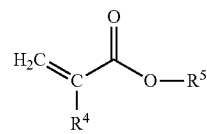
(C1)

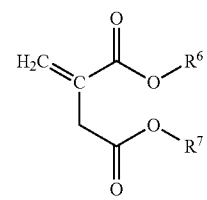
(C2)

wherein $R^4$ denotes hydrogen or a methyl group; $R^5$ denotes hydrogen or a $C_1$ to $C_4$ alkyl group; at least one of $R^6$ and $R^7$ is the group -$A^1$-$R^8$ while the other of $R^6$ and $R^7$ is hydrogen, wherein $A^1$ denotes the group *—$(CH_2CH_2O)_x$—* with x an integer from 5 to 35, the group *—$(CH_2CHMeO)_y$—* with y an integer from 5 to 35, or the group *—$(CH_2CH_2O)_x$—$(CH_2CHMeO)_y$—* with the sum of x+y an integer from 5 to 35 and x and y each not zero; and, $R^8$ is a $C_6$ to $C_{30}$ alkyl group; and
   c. optionally, polyvinyl pyrrolidone, N-vinyl pyrrolidone/vinyl acetate copolymer, or both
wherein said cosmetic agent has a viscosity of 1,000 to 500,000 mPa·s at 20° C.

13. The cosmetic agent of claim 12, wherein said polymer combination further includes the polyvinyl pyrrolidone, N-vinyl pyrrolidone/vinyl acetate copolymer, or both.

* * * * *